United States Patent [19]

Yang et al.

[11] 4,423,278

[45] Dec. 27, 1983

[54] REMOVING COLOR FROM POLYPHENYLATED ALKANE

[75] Inventors: Kang Yang; James D. Reedy; S. E. McGuire; O. C. Kerfoot, all of Ponca City, Okla.

[73] Assignee: Conoco Inc., Ponca City, Okla.

[21] Appl. No.: 436,214

[22] Filed: Jan. 17, 1983

[51] Int. Cl.³ .................................................. C07C 7/13
[52] U.S. Cl. ...................... 585/823; 585/824; 585/852; 585/868; 208/260; 208/301; 208/307
[58] Field of Search .............. 585/823, 824, 852, 868; 208/260, 301, 302, 307

[56] References Cited

U.S. PATENT DOCUMENTS

| | | | |
|---|---|---|---|
| 1,891,109 | 12/1932 | Osterstrom | 208/260 |
| 2,932,677 | 4/1960 | Kirk et al. | 585/836 |
| 3,363,020 | 1/1968 | Majewski et al. | 585/804 |
| 3,835,037 | 9/1974 | Fairweather et al. | 208/260 |
| 4,229,612 | 10/1980 | Hall, Jr. et al. | 208/307 |

FOREIGN PATENT DOCUMENTS

| | | | |
|---|---|---|---|
| 4804433 | 6/1971 | Japan | 585/823 |
| 919910 | 2/1963 | United Kingdom | 585/823 |

*Primary Examiner*—Delbert E. Gantz
*Assistant Examiner*—A. Pal
*Attorney, Agent, or Firm*—Robin M. Davis

[57] ABSTRACT

Color may be removed from colored polyphenylated alkane by contacting this material with certain adsorbants. The adsorbants provided comprise certain crystalline zeolites in a silica alumina matrix and bauxite clay having at least one material selected from the group consisting of ferric oxide, titanium oxide, and zirconium oxide, which is activated by sulfuric acid and then calcined to provide the effective adsorbant.

11 Claims, No Drawings

REMOVING COLOR FROM POLYPHENYLATED ALKANE

BACKGROUND AND FIELD OF THE INVENTION

Alkylations of benzene and other similar aromatic streams yield a polyphenylated alkane by-product. Quanities of polyphenylated alkane are collected in the bottoms part of the commerical process after the desired linear alkyl benzene is separated by distillation. Certain color causing compounds are typically contained in this polyphenylated alkane, and since no satisfactory commercial method exists for the removal of these color causing compounds, the commerical use of the polyphenylated alkane by-product is severely limited. If a satisfactory commercial method existed for the removal of the color causing compounds from polyphenylated alkane, the value and utility of this material would be enhanced. For example, it would be possible to use the clear polyphenylated alkane as a secondary plasticizer.

A variety of methods are found in the art which teach the de-colorization, of aromatic hydrocarbon streams. U.S. Pat. No. 3,729,522 teaches the preparation of low color polyphenyls which are by-products of pyrolysis. The color is removed by contact with alkali metal at a temperature of 225° C. for a sufficient amount of time. The polyphenyls can then be used as a plasticizer. U.S. Pat. No. 3,363,020 teaches the de-colorization of biphenyls by adding sulfuric acid and then distilling.

Another less pertinent method relates to purification and is disclosed in U.S. Pat. No. 2,932,677 teaching the removal color precursors from an already clear cut of alkyl aryl hydrocarbons. This process is keyed to removing color precursor compounds which are described as polynuclear hydrocarbon characterized by blue fluorescence, and which cause impure colored sulfonation product when clear, detergent quality alkyl aryl hydrocarbon was sulfonated. These color precursor bodies were removed through an oxidation treatment, followed by phase separation, followed by acid treatment and another phase separation. At this point, the patent describes the alkyl aryl hydrocarbon stream as being substantially clear. A clay treatment is then used at the termination of this process to remove the acid traces which still remain in the stream.

Another method teaching the removal of colored impurities is found in U.S. Pat. No. 3,835,037 which describes the removal of color bodies from mixed hydrocarbon feedstock containg napthlene by contacting with clay to polymerize the impurities. Distillation always follows this clay treatment to separate polymerized impurities.

The methods thus far described relate to the purification of compounds which are merely similar to the polyphenylated alkane of the instant invention. It would be beneficial to provide a cheap, simple method to remove color causing compounds which are found in the polyphenylated alkane by-product stream from alkylation reactions.

BRIEF DESCRIPTION OF THE INVENTION

Polyphenylated alkane is a by-product of alkylation reactions, and is concentrated in a bottoms portion after the desired product, linear alkyl benzene is separated by distillation. Along with the heavier polyphenylated alkane, and concentrated therein, are color causing compounds typically giving the polyphenylated alkane a dark brown color.

A method is herein provided for the removal of the color causing compounds from polyphenylated alkane comprising contacting colored polyphenylated alkane with a solid adsorbant selected from, the group consisting of (1) bauxite clays containing from about 0.1 to about 20% by weight of at least one material selected from the group consisting of ferric oxide, titanium dioxide, and zirconium oxide, said clay contacted with from about 0.1 to about 20% by weight of sulfuric acid, then activated for removal of color causing compounds by calcining the mixture at a temperature and time sufficient to activate the adsorbant prior to use, and (2) crystalline zeolite suspended in a silica alumina matrix wherein said zeolite is present in the range of from about 5% to about 20% by weight based on the total weight of the adsorbant. When colored polyphenylated alkane is contacted with the adsorbants described in this fixed bed process, color causing compounds will be removed and a clear product will result.

DETAILED DESCRIPTION OF THE INVENTION

The colored bodies giving color to polyphenylated alkane are produced in alkylation reactions and are high enough in molecular weight so that they are not taken off with the desired product in distillation. The present invention provides an effective, fixed bed method for removing these color bodies from the polyphenylated alkane stream.

The untreated colored polyphenylated alkane stream is initially a very brown color. By using the process of the instant invention, these color bodies may be removed, and the color of the polyphenylated alkane stream will progress from brown to yellow and finally to a state of extreme clarity characterized by a blue fluorescence. This fluorescence is noticable in the polyphenylated alkane stream as it becomes less colored.

One of the adsorbants used in the instant process is a bauxite clay containing at least one material from the group consisting of iron oxide, titanium dioxide, and zirconium dioxide. In order to be effective this clay must be mixed with sulfuric acid and activated by calcination at a sufficient temperature to activate the clay. The length of calcination time is not critical other than sufficiently long enough to activate the clay. An acceptable temperature range for calcination is from about 300° C. to about 700° C. A preferred calcination range is from about 500° C. to about 600° C. An acceptable amount of sulfuric acid to mix with the bauxite clay is from about 0.1 to about 25% by weight sulfuric acid, and a preferred amount of sulfuric acid is from about 5 to about 20% by weight sulfuric acid. The most preferred amount of sulfuric acid, however, is from about 10 to about 15% by weight sulfuric acid.

It has been found that the mesh size of this adsorbant can be used to optimize color removal. While any amount or size of clay particles can remove color, the activated clay should most preferably be in the mesh size range of from about 40 to about 80 U.S. standard mesh. Acceptable amounts of iron oxide, titantium dioxide, and zirconium dioxide in the bauxite clay is from about 0.1 to about 20% by weight. A preferred range is from about 5 to about 18% by weight. Suitable bauxite of the composition described occurs naturally, and is readily available. Representative but nonexhaustive examples of this clay offered commercially is Milwhit (Percolation grade) and bauxite clays.

Another adsorbant which can be used alone or in combination with the bauxite clay adsorbants, is a crystaline zeolite suspended in a silica alumina matrix. The crystaline zeolite is present in a range of from about 5 to about 20% by weight based on total weight of the adsorbants, preferably in an amount of from about 6 to about 12% by weight. The silica alumina maxtrix should acceptably have from about 10 to about 30% by weight alumina. Representative examples of suitable zeolite to be used in this adsorbant are AGZ cracking catalysts such as AGZ 50, AGZ 200, and AGZ 290, (Trademark of and sold by Davidson Chemical Company, a Division of Grace), Arocrat 425, Arocrat TS150, TS170, and T8-260 (Trademark of and sold by American Scianimid Company) and Filtral Company grade 800, and Grade 810 Crystaline Synthetic Silica Alumina. While any particle size is acceptable to remove color, the most preferred particle size is from about 40 to about 80 U.S. standard mesh. Calcination temperature acceptably is in the range of from about 700° C. to about 300° C.; a preferred range is from about 500° C. to about 600° C.

To utilize the process of the instant invention the adsorbants described are contacted with colored streams of polyphenylated alkane for a sufficient time to remove the colored compounds. This time can vary widely depending both upon the concentration of color compounds in the polyphenylated alkane stream, and upon the desired clarity in the final product. If the polyphenylated alkane is to be used as plasticizer, the American Society of Testing Materials (ASTM) color test number 1500-64 should be 1 or less. It should be noted, however, that different levels of color removal are possible to suit individual needs and desires. In order to achieve the desired level of color removal, a fixed bed process may be used. Either adsorbant or a combination of both of these adsorbants may be used in a single treatment or in sequential treatments.

Preferably, the instant invention should be utilized by passing colored polyphenylated alkane through the adsorbant at a liquid hourly space velocity (LHSV) of from about 0.1 to about 10. However, a LHSV of from about 0.5 to about 5.0 is preferred and a LHSV of from about 1 to 4 is most preferred.

The adsorbants of the instant invention are effective to remove the color from polyphenylated alkane at any convenient temperature, room temperature is satisfactory. It is preferred that the feed temperature be within the range of from about 0° to about 100° C.; and it is most preferred that the temperature be in a range of from about 25° to about 60° C.

Pressure may be maintained at any convenient level during this process. The tests of this process were carried out at atmosphereic pressure.

The process of the instant invention is more concretely described with reference to the examples below wherein all parts and percentages are by weight unless otherwise specified. The examples are provided to illustrate the present invention and not to limit it. The adsorbant used in the process of the instant invention, were prepared and were compared to other commonly used adsorbants such as silica, silica alumina, alumina, ionic exchange resin (acidic form) active carbon and zeolites alone (acidic or rare earth exchanged).

EXAMPLE

A bauxite clay adsorbant of the present invention was prepared by sulfuric acid impregnation of clay in subsequent calcination. The clay used Milwhit, percolation grade bauxite (Trademark of and sold by the Milwhit Co. Inc., 10/30 mesh) having a composition of from about 78 to about 73% by weight alumina from about 8 to about 16 percent by weight ferric oxide; from about 9 to about 6.5% by weight silica; from about 4 to about 6% by weight titanium oxide; and from about 5.5 to about 6.5% by weight volatile matter. A mixture of 20 grams of this clay with 20 grams of water and 2.5 grams of sulfuric acid was prepared as evaporated to dryness on a rotary evaporator. 12 cubic centimeters of the clay was then packed into a stainless steel tube and calcined in air at 52 cubic centimeters of air per minute for six hours at 550° C. Colored polyphenylated alkane was passed through this stainless steel tube at 30 cubic centimeters per hour and at room temperature. Initially the stream exhibited ASTM color of 2+. During 18 hours of operation, the product was collected and tested by the ASTM Test 1500-64, and had an ASTM color of 1.

The polyphenylated alkane stream used was produced as a by-product in the manufacturing of linear alkyl benzenes via chlorination-alkylation route using aluminum chloride catalyst. The alkylate used was linear having a range of carbon atoms from about 10 to about 14. The polyphenylated alkane by-product was isolated by distillation, it being the bottoms portion in a distillation which removed the mono-alkyl benzene.

The capacity of the adsorbant in this experiment was 45 volumes of polyphenylated alkane per cubic centimeter of adsorbant.

While certain embodiments and details have been shown for the purpose of illustrating this invention, it will be apparent to those skilled in this art that various changes and modifications may be made herein without departing from the spirit or scope of the invention.

We claim:

1. A method for the removal of color causing compounds from polyphenylated alkane comprising: contacting colored polyphenyated alkane with a solid adsorbant selected from the group consisting of
    (a) bauxite clays containing from about 0.1 to about 20% by weight of at least one material selected from the group consisting of ferric oxide, titanium dioxide, and zirconium oxide, said clay contacted with from about 0.1 to about 20% by weight sulfuric acid, then activated for the removal of color causing compounds by calcining the mixture at a temperature and time sufficient to activate the adsorbant prior to use, and,
    (b) crystalline zeolite suspended in a silica alumina matrix wherein said zeolite is present in the range of from about 5% to about 20% by weight of zeolite based on the total weight of the adsorbants.

2. A method as described in claim 1 wherein the adsorbant is bauxite clay.

3. A method as described in claim 2 wherein contact with the adsorbant is made for a time sufficient to remove enough color causing compounds to reduce the ASTM level to 1 or less.

4. A method as described in claim 2 wherein the calcination of the adsorbant is carried out at a temperature of from about 300° C. to about 700° C.

5. A method as described in claim 4 wherein the polyphenylated alkane is contacted with the adsorbant at a liquid hourly space velocity of from about 0.1 to about 10.

6. A method as described in claim 5 wherein the bauxite clay contains from about 0.5 to about 10% by weight iron oxide, from about 0.5 to about 10% by weight of titanium dioxide, and from about 0.5 to about 10% by weight zirconium oxide based on total weight of the bauxite.

7. A method as described in claim 1 wherein the adsorbant is a crystalline zeolite suspended in a silica alumina matrix.

8. A method as described in claim 7 wherein the silica alumina matrix contains from about 10 to about 30% by weight alumina based on total adsorbant weight.

9. A method as described in claim 8 wherein the polyphenylated alkane is contacted with the adsorbant for a time sufficient to reduce the ASTM color level to 1 or less.

10. A method as described in claim 8 wherein the calcination of the adsorbant is carried out at a temperature from about 300° C. to about 700° C.

11. A method as described in claim 10 wherein the polyphenylated alkane is passed through the adsorbant at a liquid hourly space velocity of from about 0.1 to about 10.

* * * * *